(12) United States Patent
Staalsen et al.

(10) Patent No.: US 9,757,090 B2
(45) Date of Patent: Sep. 12, 2017

(54) DEVICE FOR HOLDING AN IMAGING PROBE AND USE OF SUCH DEVICE

(75) Inventors: Niels Henrik Staalsen, Århus V (DK); Jan Jesper Andreasen, Aalborg (DK)

(73) Assignee: Region Nordjylland, Aalborg Sygehus, Aalborg O (DK)

(*) Notice: Subject to any disclaimer, the term of this patent is extended or adjusted under 35 U.S.C. 154(b) by 1269 days.

(21) Appl. No.: 13/260,198

(22) PCT Filed: Apr. 22, 2010

(86) PCT No.: PCT/DK2010/050091
§ 371 (c)(1),
(2), (4) Date: May 8, 2012

(87) PCT Pub. No.: WO2010/121626
PCT Pub. Date: Oct. 28, 2010

(65) Prior Publication Data
US 2012/0209114 A1 Aug. 16, 2012

Related U.S. Application Data

(60) Provisional application No. 61/171,557, filed on Apr. 22, 2009.

(30) Foreign Application Priority Data

Apr. 24, 2009 (DK) .................................. 2009 00527

(51) Int. Cl.
*A61B 8/00* (2006.01)
*A61B 5/01* (2006.01)
(Continued)

(52) U.S. Cl.
CPC .......... *A61B 8/4411* (2013.01); *A61B 8/0891* (2013.01); *A61B 8/4209* (2013.01);
(Continued)

(58) Field of Classification Search
CPC .......... A61B 5/01; A61B 8/06; A61B 8/0883; A61B 8/0891; A61B 8/12; A61B 8/4209;
(Continued)

(56) References Cited

U.S. PATENT DOCUMENTS 4,579,123 A * 4/1986 Chen .................... A61B 8/4281
600/459
4,794,930 A * 1/1989 Machida ............... A61B 8/4281
600/459

(Continued)

FOREIGN PATENT DOCUMENTS

EP 0 607 490 A1 7/1994

OTHER PUBLICATIONS

Dodge Jr. et al. "Lumen Diameter of Normal Human Coronary Arteries." Circulation: 86(1): pp. 232-246 Jul. 1992.*

*Primary Examiner* — Amanda Lauritzen Moher
(74) *Attorney, Agent, or Firm* — Knobbe Martens Olsen & Bear, LLP

(57) ABSTRACT

The present invention relates to the field of e.g. ultra-sound imaging. In particular the present invention relates to a device for supporting an ultrasound probe or probe with other contrast imaging technology, preferably during heart imaging. The device comprises a fixation part comprising an aperture for receiving the probe. The device also comprises at least two skin supports (2, 3) for supporting the probe against a tissue of a human or animal bodily organ. The fixation part is positioned above the skin supports and a cavity (4) between the skin supports (2,3) are provided for allowing the probe to perform measurements of the organ. In addition the invention relates to a handle for operating the device a system comprising a probe, the device and the handle.

13 Claims, 11 Drawing Sheets

(51) Int. Cl.
  *A61B 8/06* (2006.01)
  *A61B 8/08* (2006.01)
  *A61B 8/12* (2006.01)

(52) U.S. Cl.
  CPC .......... *A61B 8/4281* (2013.01); *A61B 8/4455* (2013.01); *A61B 5/01* (2013.01); *A61B 8/06* (2013.01); *A61B 8/0883* (2013.01); *A61B 8/12* (2013.01)

(58) Field of Classification Search
  CPC ... A61B 8/4281; A61B 8/4411; A61B 8/4455; A61B 8/4472; A61B 8/488; G10K 11/004; G10K 11/352; A61N 7/00; F15B 21/06; F15C 5/00; F16K 99/0001; F16K 99/0057; F25B 2309/61; F25B 2400/15; Y10S 128/915; Y10T 137/3662
  See application file for complete search history.

(56) References Cited

U.S. PATENT DOCUMENTS

| | | | | |
|---|---|---|---|---|
| 4,796,632 A | * | 1/1989 | Boyd | A61B 8/4281 600/459 |
| 4,867,169 A | * | 9/1989 | Machida | G10K 11/02 600/446 |
| 4,920,966 A | * | 5/1990 | Hon | A61B 5/4356 600/459 |
| 4,947,853 A | | 8/1990 | Hon | |
| 5,078,149 A | * | 1/1992 | Katsumata | A61B 8/4281 600/459 |
| 5,094,243 A | * | 3/1992 | Puy | A61B 8/4209 600/459 |
| 5,575,291 A | * | 11/1996 | Hayakawa | C08J 3/075 600/459 |
| 5,931,786 A | * | 8/1999 | Whitmore, III | A61B 8/12 600/459 |
| 6,080,108 A | * | 6/2000 | Dunham | A61B 8/08 600/459 |
| 6,210,336 B1 | * | 4/2001 | Fredriksen | A61B 8/4281 600/459 |
| 6,261,231 B1 | | 7/2001 | Damphousse et al. | |
| 6,406,424 B1 | * | 6/2002 | Williamson et al. | 600/201 |
| 7,149,566 B2 | * | 12/2006 | Lee | 600/429 |
| D724,745 S | * | 3/2015 | Orome | D24/186 |
| 2003/0195420 A1 | | 10/2003 | Mendlein et al. | |
| 2003/0233022 A1 | * | 12/2003 | Vidlund | A61B 17/00234 600/16 |
| 2004/0054288 A1 | * | 3/2004 | Nygaard | A61B 8/12 600/459 |
| 2004/0064051 A1 | | 4/2004 | Talish et al. | |
| 2004/0087851 A1 | | 5/2004 | Lee | |
| 2005/0182431 A1 | * | 8/2005 | Hausen | A61B 17/11 606/153 |
| 2005/0240102 A1 | * | 10/2005 | Rachlin | A61B 8/10 600/437 |
| 2006/0079782 A1 | * | 4/2006 | Beach | A61B 5/02007 600/450 |
| 2007/0033735 A1 | * | 2/2007 | Formenti | 5/600 |
| 2008/0208060 A1 | * | 8/2008 | Murkin | A61B 8/06 600/459 |

\* cited by examiner

DEVICE FOR HOLDING AN IMAGING PROBE AND USE OF SUCH DEVICE

CROSS REFERENCE TO RELATED APPLICATIONS

This application claims the benefit and priority to and is a U.S. National Phase Application of PCT International Application Number PCT/DK2010/050091, filed on Apr. 22, 2010, designating the United States of America and published in the English language, which is an International Application of and claims the benefit of priority to U.S. Provisional Application No. 61/171,557, filed on Apr. 22, 2009, and Danish Patent Application No. PA 2009 00527, filed on Apr. 24, 2009. The disclosures of the above-referenced applications are hereby expressly incorporated by reference in their entireties.

TECHNICAL FIELD OF THE INVENTION

The invention relates to the field of e.g. ultrasound imaging. In particular the invention relates to a device for supporting an ultrasound probe or a probe with other contrast imaging technology, preferably during coronary imaging. The invention also relates to uses of such, e.g., ultrasound imaging technology.

BACKGROUND OF THE INVENTION

Ultrasound imaging and/or other contrast imaging is commonly performed by a clinician using a hand held probe which is positioned adjacent to a patient. However, the effective use of a hand held probe is limited by frame-to-frame variability in the images produced, occupational health hazards, and the inability to monitor an organ of interest during exercise induced stress. These limitations can seriously and deleteriously affect the utility of the ultrasound/contrast imaging technique.

Frame-to-frame variability in the images arises from movement of the probe between successive images. To minimize distortions resulting from frame-to-frame variability, the probe must be maintained in a steady orientation relative to the patient. For example, when imaging a patient's heart, 5 to 10 cardiac cycles are typically needed for contrast myocardial perfusion to occur before the next ultrasound wave is emitted. Since a cardiac cycle typically is about 1 second in duration, a clinician must be able to steadily hold a probe for 5 to 10 seconds between successive e.g. ultrasonic emissions. Movement of the probe during that time period will result in frame-to-frame variability between images and cardiac views obtained.

U.S. Pat. No. 6,261,231 B1 discloses an apparatus for holding a probe and a method for using the same. The apparatus comprises a body portion having a longitudinal bore and a membrane holder positioned over a first end of the body portion. The membrane holder defines an aperture which is covered by a membrane. A receptacle for receiving the probe is rotatably positioned within the longitudinal bore of the body portion at a second end of the body portion. The membrane, membrane holder, body portion, receptacle, and probe define a sealed chamber for containing a contacting medium.

US 2003/0195420 A1 discloses a probe holder for reducing medical probe contamination. The probe holder comprises a holder for an ultrasonic probe adapted for skin-interrogation of tissues subjacent to a skin interrogation site. The holder is adapted to fit at least an interrogation surface of said ultrasonic probe, and the holder includes a securing portion for securing said holder to said ultrasonic probe and an interrogation window in acoustic alignment with at least a section of said interrogation surface, and a sono-lucent film covering said interrogation window.

US 2004087851 discloses an apparatus for orienting and maintaining the orientation of soft tissue, comprising: a frame defining an opening, the frame configured to orient and immobilize an area of soft tissue positioned on one side of the opening; an attachment mechanism to secure the frame to an attachment region defined by the area of soft tissue or by a skin surface overlying the area of soft tissue, to facilitate orienting and immobilizing the area of soft tissue; and an imaging device to image the area of soft tissue.

US 2008208060 discloses an acoustic coupler for use with an ultrasound probe by a surgeon as a diagnostic tool. The invention provides an acoustic, coupler for use with an ultrasound probe for imaging an anatomical structure, comprising a member that is capable of being sterilized, is acoustically neutral, and is in vivo biocompatible, and comprises: (a) a first surface adapted to receive and fix the position of an ultrasound probe head relative to the member, to ensure the correct orientation of the probe head in relation to the anatomical structure during imaging: and (b) a second surface opposed to the first surface, the second surface being shaped to substantially conform to the contour of the anatomical structure.

An improved means for improving imaging of a bodily organ of a human or an animal such as of the heart would be advantageous, and in particular a more efficient and/or reliable and/or expedient means and use would be advantageous.

SUMMARY OF THE INVENTION

The technical quality of anastomoses during coronary artery bypass grafting is often evaluated by measuring flow rate in grafts using transit time flowmetry. Unfortunately, flow rate and flow waveform are poor indicators of the anatomy of anastomoses. Up to 9% of the anastomoses may have a stenosis of 50% not detected by flow measuring techniques.

A better way to evaluate the anatomy of an anastomosis is 3-dimensional imaging. High-frequency epicardial echocardiography has the spatial and temporal resolution to produce a clear image of the anastomoses, detect intramural vessels and ensure the optimal place for grafting. (Phantom resolution of 6.5-15 MHz transducers is reported in the range of 0.1 mm to 2.5 mm, with approximately 4 cm penetration depth). Based on ex vivo porcine and human hearts, epicardial high-frequency echocardiography has a high sensitivity (0.98) and specificity (1.0) for detection of anastomotic construction errors.

Problems concerning intra-operative epicardiac echo-examinations and flow-visualizations of coronary arteries and coronary anastomoses are:

a) It is difficult to obtain stable imaging when the heart is beating, thus impeding the reading of the image obtained by the e.g. ultrasonic probe.

b) It is difficult to obtain good acoustic contact between the probe and e.g. coronary arteries, possibly air may be entrained there-between.

c) When the probe is positioned on e.g. a vessel-stitching, pressure is applied to the area and which may invalidate or reduce certainty of the measurements.

d) During open heart surgery, time is an important factor, problem a)-c) slows down the possibility of obtaining fast measurements.

Thus, an object of the present invention relates to a device for holding a probe. One object of the device may be to be able to hold the probe steady during measurements. Another object of the device may be to hold the probe at locations where holding the probe by hand may be difficult. Still another object of the device may be to hold not only the probe but also possible auxiliary equipment used together with the probe at a location for measurements by the probe.

Thus, one aspect of the invention relates to a device for holding a probe comprising a fixation part comprising an aperture for receiving the probe, at least two skin supports for supporting the probe against a tissue of a human or animal bodily organ and wherein the fixation part is positioned above the skin supports, and wherein a cavity between the skin supports are provided for allowing the probe to perform measurements of the organ.

The term "probe" as used herein refers to any ultrasound probe or probe with other contrast imaging technology which can be mounted in the device of the invention. Non-limiting examples of probes are ultrasonography probes (echoprobes), which e.g. can be used for imaging and flow-visualization of coronary arteries, bypass grafts and anastomoses on beating and relaxed hearts e.g. during coronary bypass operations.

The term "aperture" as used herein refers to a three-dimensional void of the device and in which a probe can be positioned. The shape and size of an aperture can be adapted to a specific probe of a specific imaging apparatus. An aperture may comprise one or more means for maintaining the probe in the device.

The term "cavity" in the present context refers to a cavity in the device intended for receiving part of the "organ" to be examined. An example of an organ is a graft positioned on a heart after a by-pass operation.

Ultrasound images are operator dependent, but intraoperative echocardiography of coronary anastomoses using an ultrasound transducer positioning device according to the invention makes it easy and reproducible to use in all coronary territories. The device according to the invention has the advantage of stabilizing an ultrasound transducer thereby obtaining optimal acoustical contact and without deforming the anastomosis on, e.g., a beating, and thus pulsating, heart.

In another aspect the invention relates to a device for examining an organ, said device comprising
 a first fixation part comprising an aperture 5 for receiving a probe 9,
 at least two skin supports 2, 3 for supporting the device, and the probe when positioned in the device, against a tissue of a human or animal bodily organ, and
 a cavity 4 between the skin supports 2,3, wherein
the fixation part is positioned above the skin supports 2,3 relative to the tissue of the human or animal body organ when the device is being used, and
the cavity 4 is spatially defined by the two skin supports 2,3 and at least one opening 6 or 7,
  said at least one opening being provided between the at least two skin support 2, 3, and
  said at least one opening intended for accommodating part of the organ to be examined.

The device according to the invention relates to a device (e.g. an ultrasound transducer), which can 1) stabilize the involved part of e.g. the myocardium on beating heart, 2) keep the gel at place and 3) position a probe (e.g. an ultrasound transducer) correct for imaging in the anterior-posterior (AP) and left-right (LR) planes without deforming the anastomosis studied. These are all problems which previously were obstacles for receiving reliable images from e.g. grafts.

Thus, using the device of the present invention may enable the user of the probe to
1. locate the coronary arteries of heart, which is often hidden in fatty tissue or located inside the muscular tissue of the heart,
2. assess how large an artery is (is it big enough for providing a bypass graft),
3. control the stitching between the new graft and the coronary artery of heart—is the stitching open, is it contracted or is it perfect?,
4. stabilize the area of a heart which is going to be examined, while the heart is still beating (image-output from e.g. an ultrasonic probe is "stabilized"),
5. optimize the acoustic contact between the probe and the area to be examined (areas like heart muscles, bypass grafts, anastomoses, and coronary vessels), and
6. keep the probe locked in the device at a stable distance from the target area without deforming the target area such as tissue of the heart.

Openings

As described above, in certain instances only one opening intended for accommodating part of the organ to be examined is necessary. This is the case where the part of the organ is not a continues part and the organ can therefore be fully surrounded with one opening without putting pressure on the organ to be examined. In many instances two opening may be provided to fully accommodate the organ to be examined. Thus in an embodiment the device comprises at least two openings 6, 7, said at least two openings being provided opposite each other with the one opening provided between the at least two skin supports at a proximal end of the supports, and with the other opening also provided between, the at least two skin supports, at a distal end, opposite to the proximal end, of the supports. This embodiment may find its use when part of a graft on a beating heart is to be examined.

The cavity 4 is defined by the two skin supports and the two openings 6, 7. The openings 6, 7 may accommodate better positioning of e.g. grafts which due to their structure need the openings 6 and 7 for optimal positioning of the probe holder and thus better imaging. Thus, in an embodiment the sides of the aperture 4 are defined by the two skin supports 2, 3 and the two openings 6 and 7. The two skin supports may be positioned parallel to each other. It is to be understood that aperture 4 according to the invention may not be entirely straight, but may also be shaped after specific types of grafts which requires a differently shaped cavity e.g. curved.

In another embodiment the invention relates to a device comprising at least two openings 6, 7, said at least two openings being provided opposite each other with the one opening provided in one of the at least two skin supports and with the other opening provided at another, opposite to the one, of the at least two skin supports.

Distance Between Skin Supports

It may also be difficult to monitor a specific bypass graft, because the width of such grafts may vary. Thus, according to a possible embodiment, the skin supports are positioned parallel to each other with a mutual distance of between 3 mm to 50 mm, such as 3 mm to 40 mm, such as 8 mm to 40 mm, such as 8 mm to 30 mm, such as 5 mm to 20 mm, such as 5 mm to 15 mm and where a cavity is provided between the supports.

An advantage of having different sizes between the skin supports is that bypass grafts used together with the device according to the invention may vary in size. Thus, to have a fit of the bypass graft between the skin supports, different sizes may have to be available. Another advantage may be that any gel used together with a probe is kept at the site of imaging.

Other types of grafts (or other areas of tissue or other organ which is be examined) may have shapes which make it undesirable that the skin supports are positioned parallel to each other. Thus, the design of the skin supports and the cavity between them may vary to fit other shapes and sizes of tissues and/or organs which are to be examined using the device of the invention.

Height of Skin Supports

It may also be difficult to monitor a specific bypass graft, since not only the width of such bypass grafts varies, but also the height of such bypass grafts may vary.

Thus, in a possible embodiment a height of the skin supports 2, 3, at least along the cavity 4, is between 1 mm and 10 mm, preferably between 1 mm and 5 mm. By having the probe supported exactly over e.g. a bypass graft, no pressure is applied directly on the graft, which otherwise may be harmful to the graft and it may also result in invalid data collection. Furthermore, e.g. ultrasonic acoustic contact between the probe and the target area is optimized.

Protrusions

To be able to hold the probe in the device during imaging, means for holding is preferably present in the device.

Thus, in a possible further embodiment, the aperture comprises one or more protrusions or notches for holding the probe in the aperture. Different means for holding a probe in the device is available. In one embodiment of the invention, the protrusions are one or more beads extending into and along the aperture in one or more planes. In another embodiment, the invention relates to a device, wherein the protrusions 1 are one or more beads 1 or the notches are one or more grooves extending along side walls of the device, said side walls forming the aperture 5 of the device. Different probes, possible for different imaging equipment, may have different sizes, which may result in pressure on a graft and/or poor acoustic contact between the probe and the target area. Thus, the precise shape of the aperture of the device can be shaped to fit different types of probes. The person skilled in the art would know how to adjust other parameters such as the size of the aperture.

Longitudinal Axis Imaging

It may be advantageously that the device is adapted to allow different types of images. Thus in an embodiment the cavity is positioned longitudinally to an intended displacement of the probe when imaging the organ, said cavity having an aperture for the probe at a front side location of the device. By having the cavity longitudinally to the aperture for the probe, longitudinal sectional images in different planes may be obtained. Thus, in an embodiment the invention relates to a device, wherein the cavity 4 is oblong with a longitudinal axis of the cavity positioned longitudinally to an intended direction of displacement of the probe when imaging the organ.

Transversely Axis Imaging

In another embodiment, the cavity is positioned transversely to an intended displacement of the probe when imaging the organ, said cavity having an aperture for the probe at a sideway location of the device. In a further embodiment the cavity 4 is oblong with a longitudinal axis of the cavity positioned transversely to an intended direction of displacement of the probe when imaging the organ. By having the aperture positioned sideway to the skin supports, transverse images in different planes may be obtained. It may also be possible to provide a device allowing for both longitudinal sectional imaging and transverse sectional imaging. This may be done by having a larger cavity and or a larger opening.

Probe Direction Re. Device Orientation

In a possible embodiment of the device according to the invention the device is capable of holding the probe in a first direction where an imaging plane of the probe is substantially parallel with the oblong cavity. When imaging, it may be advantageous that the imaging plane of the probe coinsides with the orientation of the oblong cavity. Thus, when imgaing, the imaging plane of the probe will be substantially parallel to the longitudinal orientation of the device, nondepent on the orientation of the apertures in the cavity. Whether the orientation mentioned, i.e., the imaging plane substantially parallel with the oblong cavity, is an advantage depends on the organ being imaged and on the type of probe.

In a possible other embodiment of the device according to the invention the device is capable of holding the probe in a second direction where an imaging plane of the probe is substantially transversal to the oblong cavity. When imaging, it may be advantageously that the imaging plane of the probe coinsides with the orientation of the oblong cavity. Thus, when imgaing, the imaging plane of the probe will possibly be perpendicular to the longitudinal orientation of the device, nondepent on the orientation of the apertures in the cavity. Whether the orientation mentioned, i.e., the imaging plane transversal to the oblong cavity, is an advantage depends on the organ being imaged and on the type of probe.

In a possible third embodiment, the one and same device is capable of holding the probe, by choice of an operator, either in a first direction where an imaging plane of the probe is substantially parallel with the oblong cavity or in a second direction where an imaging plane of the probe is transversal to the oblong cavity. An embodiment incorporating the possibility, in the one and same device, of holding the probe both so that the imaging plane is substantially parallel with and so that the imaging plane is transversal to, preferably perpendicular to, the oblong cavity, gives an operator different opportunities of imaging the organ or part of the organ.

Transparency

It may be difficult for the surgeon using the device of the invention to position the device on an exact position on a heart, because the device may visually conceal the target area. Thus, in a possible embodiment at least part of the device is transparent to the human eye, preferably all of the device being transparent to the human eye, for enabling locating the device towards the organ.

By having the device made at least partly transparent to the human eye, the surgeon or other medical personnel using the device may more easily correctly position the device on the tissue of the organ. It is to be understood that the device may made fully transparent or at least made 30% transparent material such as 40%, or 50%, 60%, 70%, 80%, 90%, or such as 100% transparent.

Inlet for Gel

It may be an advantage to be able to apply more gel during an image session since the gel may be displaced during imaging. Thus, in an embodiment according to the invention, said device intended for an ultrasonic probe and said device comprising an inlet to the cavity for adding a gel, said inlet being in fluid communication with a reservoir for the gel, said reservoir for the gel being remotely placed in relation to the cavity. Such a connection may allow for adding more gel under the device, without having to remove the device from the tissue. In this way faster and more reliable results may be obtained. It is of course to be understood that the inlet of the device may be coupled to the gel reservoir through a tube. In an embodiment the outlet is positioned in the cavity between said tissue supports. In another embodiment the outlet is positioned at the bottom side of at least one of the skin supports. Thus, in an additional embodiment the device comprises more than one outlet such as 2, 3, 4 or more outlets. By having more than one outlet positioned either at the sides of the cavity 4 or the bottom side of the skin supports, a more homogenous distribution of the gel may be obtained.

Handle

During imaging under e.g. open heart surgery, it may be necessary to obtain images from locations which are difficult to get accession to. In addition little space may be available during surgery requiring compact equipment. Thus, in a further embodiment, the invention relates to a device according to any of the preceding claims, said device comprising a handle, wherein said handle is arranged for operating said device when connected to a probe, and where said handle is provided with at least one of the following conduits from a location remote from the device: at least one conduit for passing electronic signal wires from the remote location to the probe, at least one conduit for passing gel from the remote location to the cavity, at least one conduit for passing optical signal wires from a remote location to an optical element connected to the device together with the probe. By having a handle positioned on the device, easier accession to difficult location may be obtained. In addition by letting the handle comprise one or more conduits, such as for passing gel to the device more space is freed to allow the surgeon to work.

The handle may be fixed to the device by different mechanisms. Thus, in an embodiment the connections means are a second aperture positioned at the outer side of the device 10. Besides being able to connect to the device it may also be an advantage if the handle could be released after use. Thus, in a further aspect the invention relates to a handle 8 for operating a device 10 said handle comprising means for releasable attaching the handle to the device (10), said means comprising a clip to be fixed to the probe, said clip having at least two gripping arms, said at least two gripping arms intended for cooperating with corresponding grooves of the probe. As mentioned previously it may be an advantage if the handle also comprised further features. Thus, in an additional embodiment said handle being provided with at least one of the following conduits from location remote from the device: at least one conduit for passing electronic signal wires from the remote location to the probe, at least one conduit for passing gel from the remote location to the cavity, at least one conduit for passing optical signal wires from a remote location to an optical element connected to the device together with the probe. Again this may allow for more visual contact to the organ to be examined and thereby provide a saver procedure.

System

The device and the handle according to the invention may form part of a operating system together with a probe. Thus, in an additional aspect the invention relates to a system for examining an organ, said system comprising a probe,
a device according to the invention, and
a handle according to the invention.

This system allows for more precise measurements and save use during surgery.

In a more specific embodiment the invention relates to a system, wherein the probe 9 is an ultrasound imaging unit, wherein the cavity of the device is provided with at least two openings for accommodating a graft of a cardiologic bypass, and where the handle is provided with a clip to be releasable fixed to the probe. Ultrasound images are operator dependent, but intraoperative echocardiography of coronary anastomoses using the device or system according to the invention has the potential to be reproducible and is relatively easy to use in all coronary territories.

Use of Device

In an additional aspect the invention relates to use of a device 10 according to the invention for holding a probe 9 selected from the group consisting of: ultrasound imaging equipment, blood flow measuring equipment and a thermometer.

During use of the device different organs may be examined. Thus, in yet an aspect, the invention relates to use of according to the invention, for providing imaging of a human or animal organ selected from the group of: the heart, coronary veins and/or arteries or other organs exhibiting pulsation during imaging.

BRIEF DESCRIPTION OF THE FIGURES

The invention will be described in further detail referring to the figures, where.

DETAILED DESCRIPTION OF THE INVENTION

Figure 1:
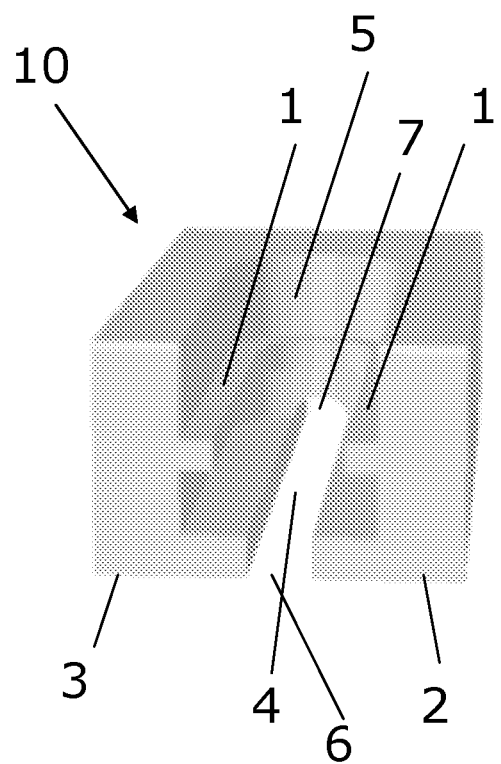
FIG. 1-3 show schematically an embodiment of the invention, wherein a device for holding a probe for longitudinal sectional imaging is shown.
Figure 2:
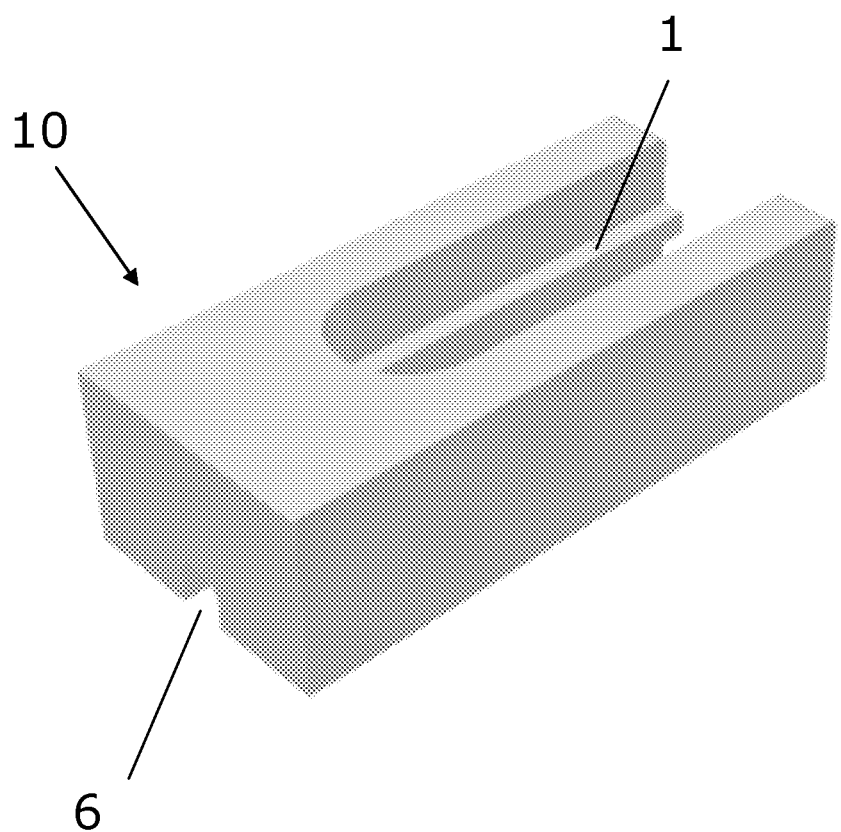
Figure 3:
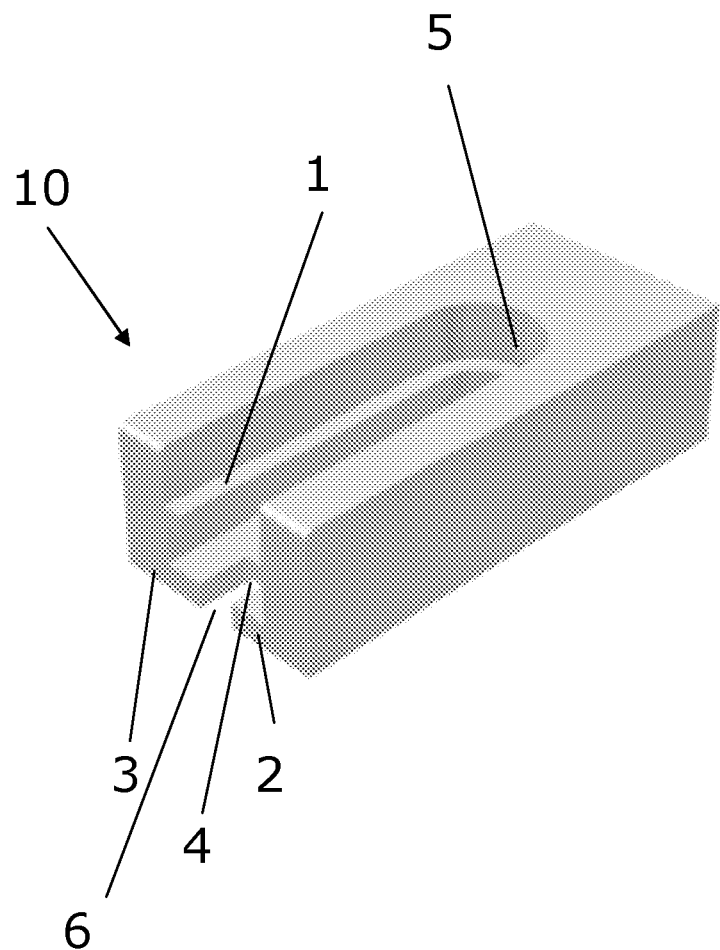

FIG. 1-3 show an embodiment of a device comprises two skin supports 2, 3 which are intended for being positioned against a tissue, e.g. of a beating, and thus pulsating, heart. The skin supports 2, 3 stabilize the area of which imaging is required. The skin supports 2, 3 also stabilize abutment of a probe (see FIG. 10 and FIG. 11) at the area of which imaging is required. The shape and size of the skin supports 2, 3 may vary, depending on the tissue, the organ and/or the size of the tissue area on which the device is to be positioned.

Between the skin supports 2, 3 a cavity 4 is provided. The cavity 4 accommodates e.g. a bypass graft, heart muscles, anastomoses and coronary vessels. In the detailed description of the invention reference is made to the heart as the organ and to different parts of the heart for the cavity 4 to accommodate. However, this should not be construed as limiting the invention to imaging of the heart. Other organs and parts of other organs may also be accommodated by the cavity 4.

Since bypass grafts may vary in size, the distance between the skin supports 2, 3 may vary. Also the height of bypass grafts may vary. Thus, to obtain a good imaging contact between a graft and the probe, the height at which the probe (see FIG. 10 and FIG. 11) is supported along the inner sides of the skin supports 2,3 may vary. Furthermore, the shape of the device also has the advantage that any gel used together with a probe is kept between the skin supports 2,3 at the site of imaging. In addition, the cavity 4 is also necessary for allowing the probe to obtain imaging since direct contact between the tissue and the probe is to be avoided. It is to be understood that the cavity 4 does not need to extend along a straight line but may also have different shapes, such as extending along a curved line, to accommodate e.g. a graft with a different shape.

The cavity 4 is defined by the two skin supports and the two openings 6,7. The openings 6,7 may accommodate better positioning of. e.g, grafts which due to their structure need the openings 6 and 7 for optimal positioning of the probe holder and thus better imaging. Thus, in a possible embodiment, the sides of the aperture 4 are defined by the two skin supports 2,3 and the two openings 6 and 7. The two skin supports may be positioned parallel to each other.

The device also comprises an aperture 5 for receiving the probe used together with the device. The size and shape of the aperture may vary depending on the exact shape and size of the probe to be used together with the device. To make sure that the probe is properly secured in the device, the device may comprise fixing elements 1 for securing the probe to the device. Examples of fixing elements 1 are one or more protrusions or notches inside the aperture, and into which protrusions or notches the probe can displaced, thereby holding the probe in the device. The shape and size of such protrusions or notches may vary. In the embodiment shown, protrusions in the shape of beads are provided.

The positioning of the cavity 4 in the device may vary depending on which type of probe and which type of imaging is intended.

For obtaining longitudinal sectional images, the cavity 4 may be positioned longitudinally to the aperture 5 (FIGS. 1-3) for receiving the probe.

Figure 4:
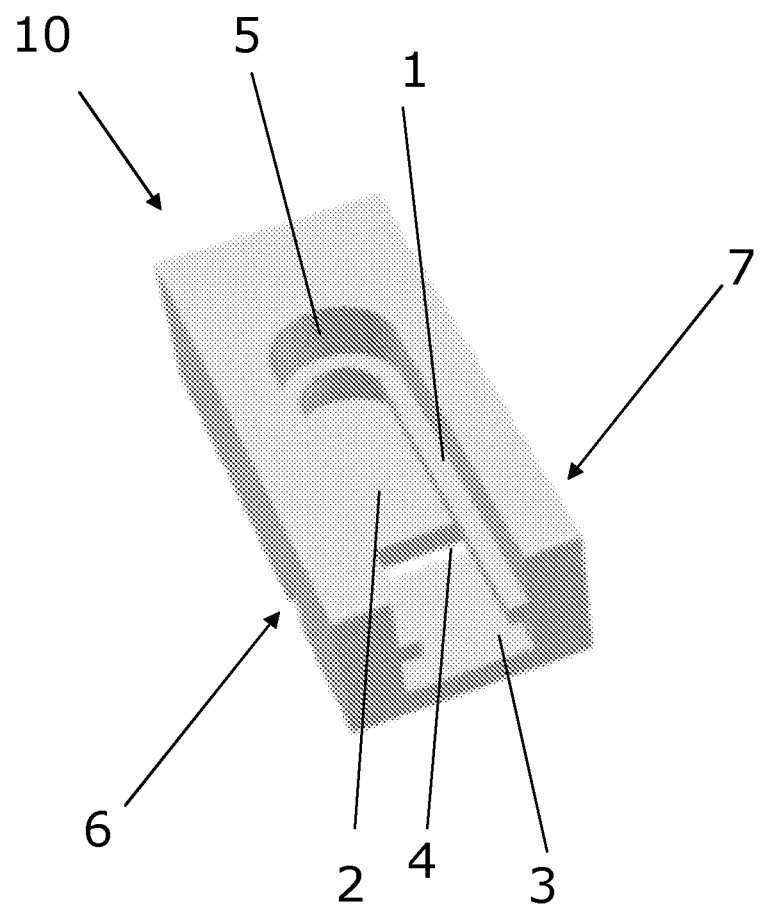
FIG. 4-5 show schematically an embodiment of the invention, wherein a device for holding a probe for cross-sectional imaging is shown.
Figure 5:
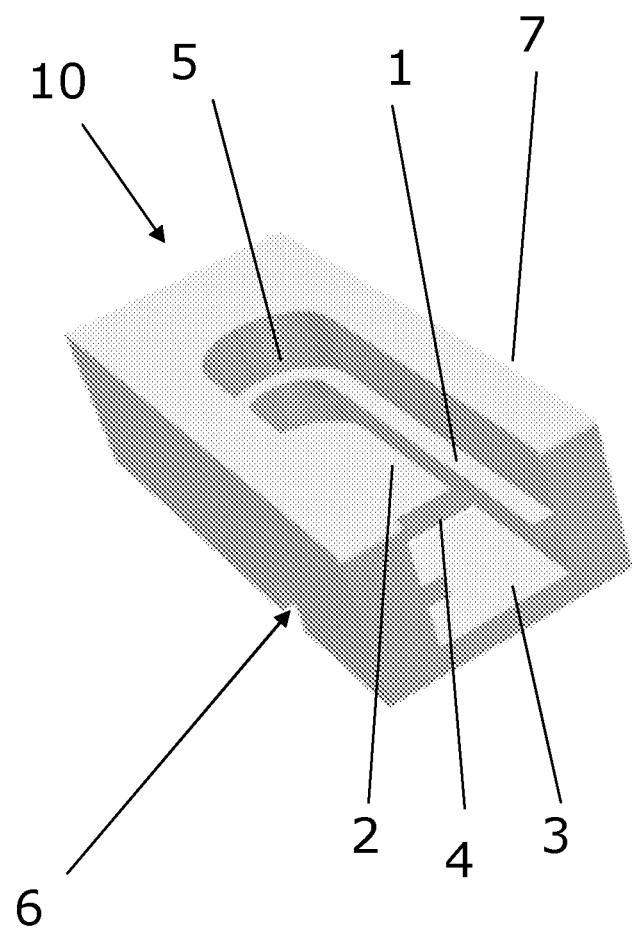
Figure 6:
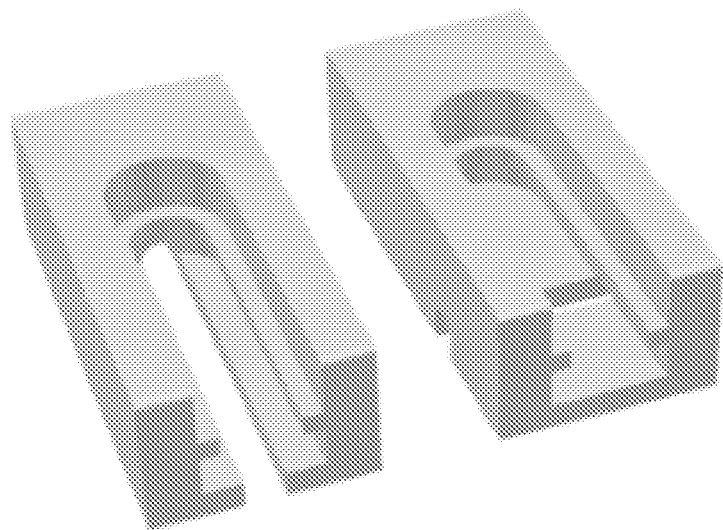
FIG. 6 shows schematically the two embodiments of FIG. 1-3 and FIG. 4-5, respectively, of the invention.

For obtaining transversal images, the cavity 4 may be positioned transversely to the aperture 5 for receiving the probe (see FIGS. 4-5).

The device is to be carefully positioned on possibly very sensitive tissue, and therefore correct positioning of the device and thus of the probe itself is essential. Therefore, it may be advantageous if at least part of the device is transparent. The device may also be made entirely of transparent material. Different types of transparent materials may e.g. be used for the device, e.g. polycarbonate.

Figure 7:
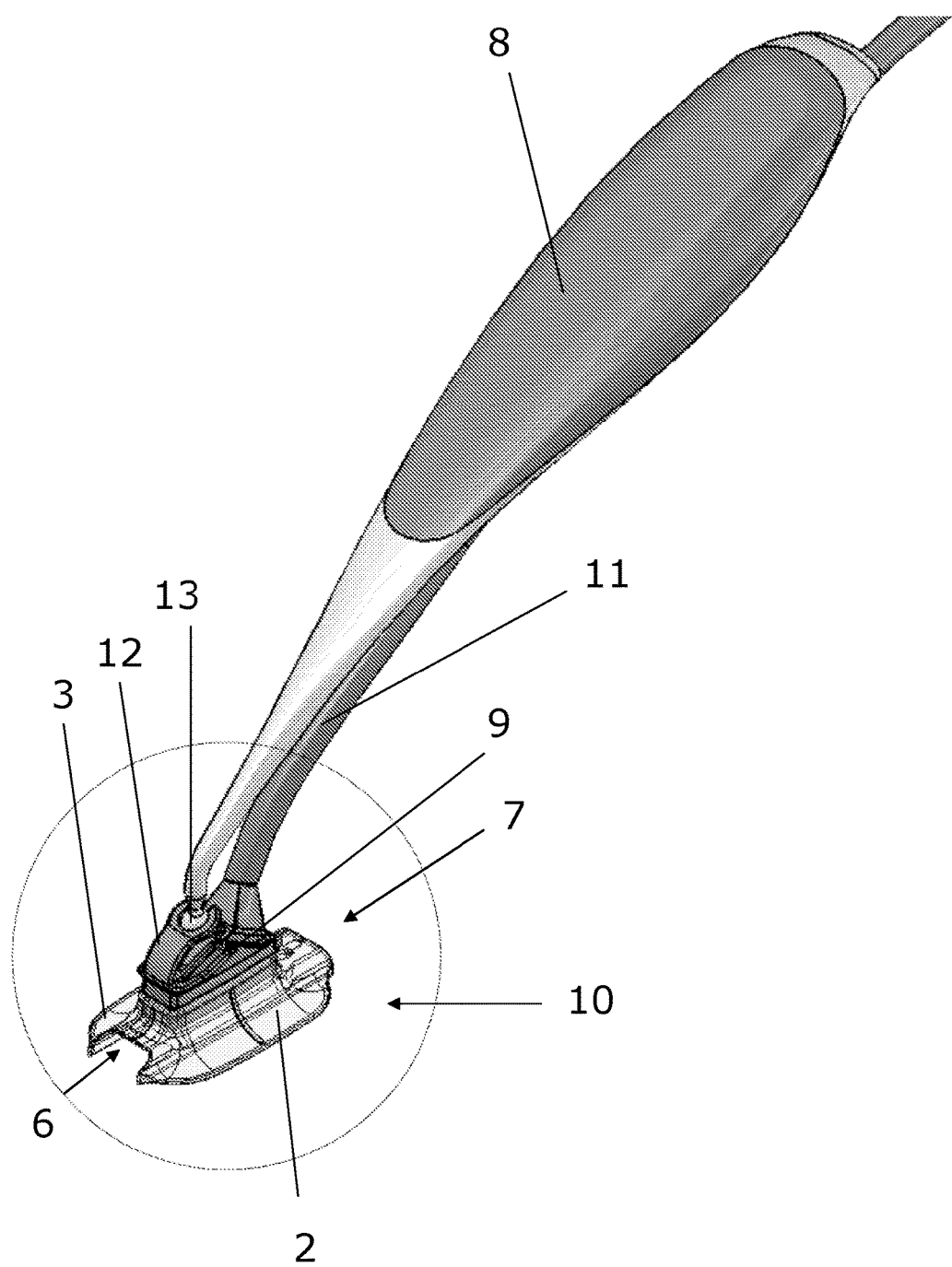
FIG. 7-9 show an embodiment of the system according to the invention comprising the device 10, the probe 9 and the handle 8.
Figure 8:
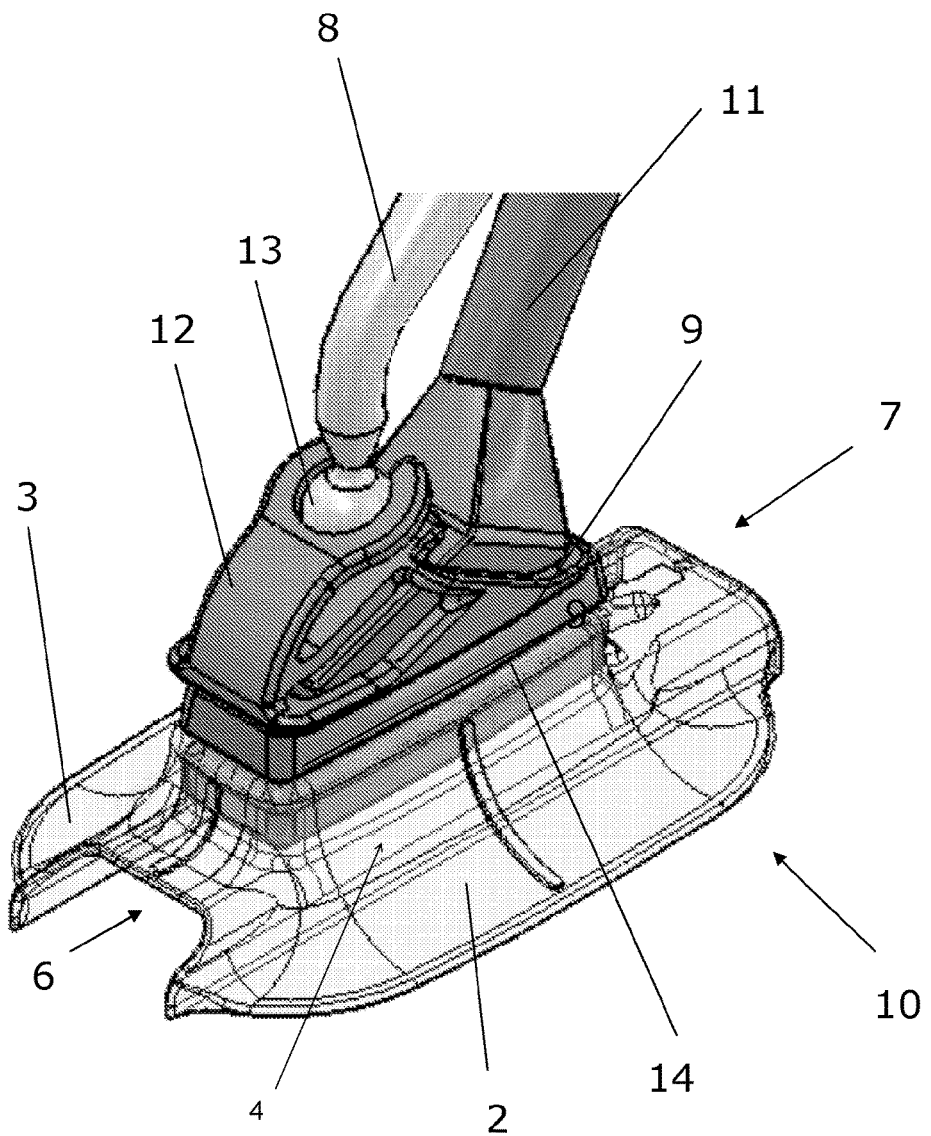
Figure 9:
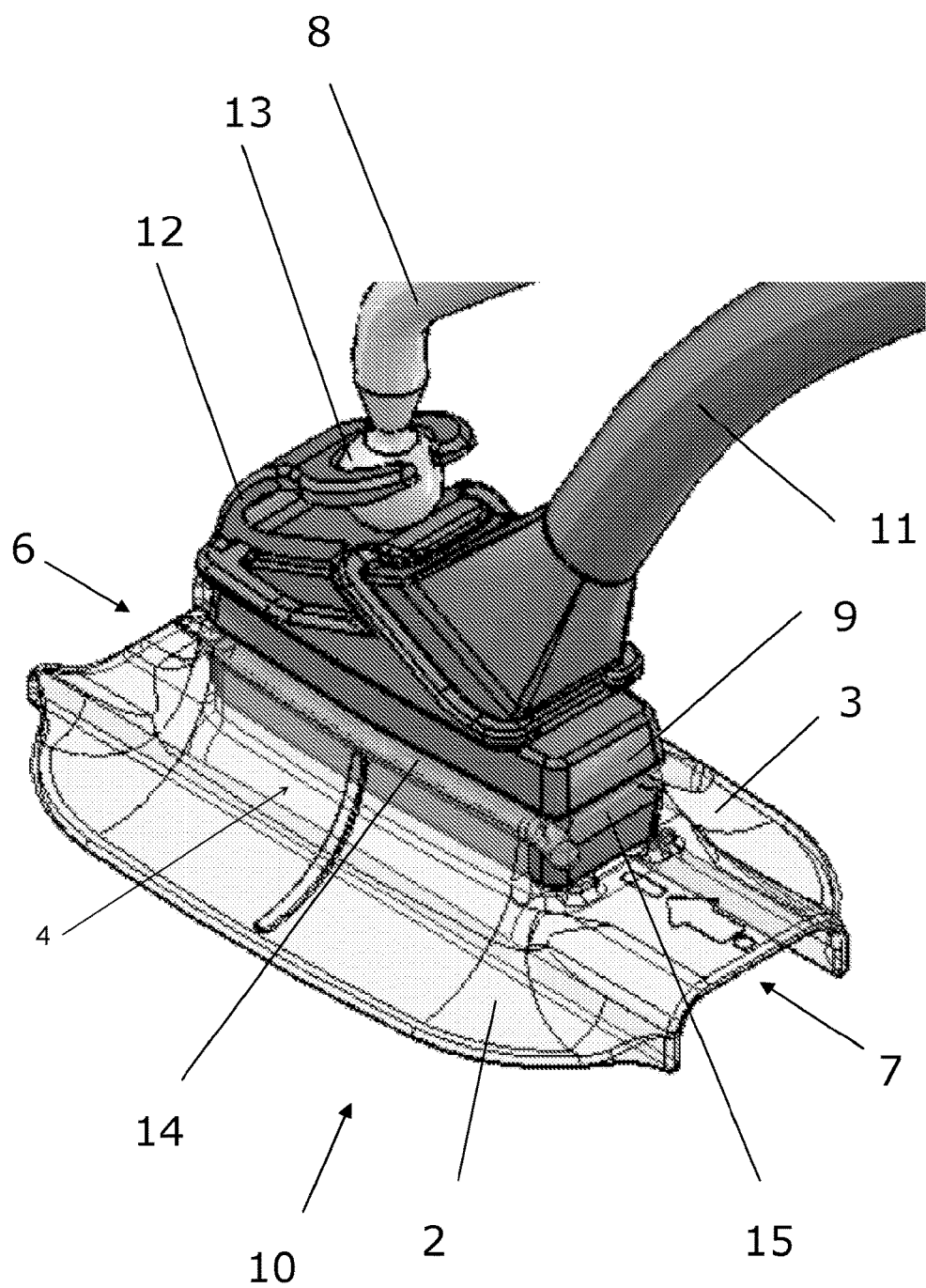

FIG. 7-9 show an embodiment of the system according to the invention. The handle 8 may be attached directly to the device 10, but it may also be attached to the probe 9. The advantage of providing a handle 8 may be that it allows for operating the device when access to the area to be imaged is difficult to reach. This may often be the case during open heart surgery. The advantage of providing a handle 8 may additionally or alternatively be that gripping the probe 9 is made easier if perhaps the shape of the probe itself is difficult to hold. Preferably, wiring or tubing 11 to the probe 9 or to the device 10 may be positioned inside or along the handle 8. Wiring may be electric wiring to the probe, or it may also be other measuring equipment to be directed to the point to be imaged. By providing wiring along the handle 8, any wires will be bundled during imaging. Tubing may be a tube for providing gel to the cavity 4 of the device. The gel is provided during ultrasound imaging for proving better transmission of ultrasound waves than through air. By providing a tube 11 along the handle 8, the gel may be applied from a remote location.

In the embodiment shown, the handle 8 is provided with attachment means in the shape of a clip 12 for releasable attaching the handle 8 to the device 10. The clip 12 is attached to the handle 8 via a swivel-connection 13. The clip 12 is fixed to the probe 9 by means of two gripping members 14. Thereby, a releasably and adjustable connection between the handle 8 and the probe 9 is provided. The gripping members 14 of the clip 12 are inserted into a corresponding groove 15 (see FIG. 9) of the probe 9, said grove extending along the circumference of the probe 9. The groove is part of the probe 9, provided independently of the use of the probe 9 together with the device 10 according to the present invention.

Other means for attaching the probe to the handle 8 may be provided. Alternatively to gripping members and a groove, notches of the probe and corresponding recesses of the device, or vice versa, may be provided.

In the embodiment shown, the groove 15 of the probe 9 is also used for attaching the device 10 to the probe. Thus, the device 10 has an upper aperture (not visible in FIG. 7-9) corresponding to the shape of the groove of the probe 9.

Figure 10:
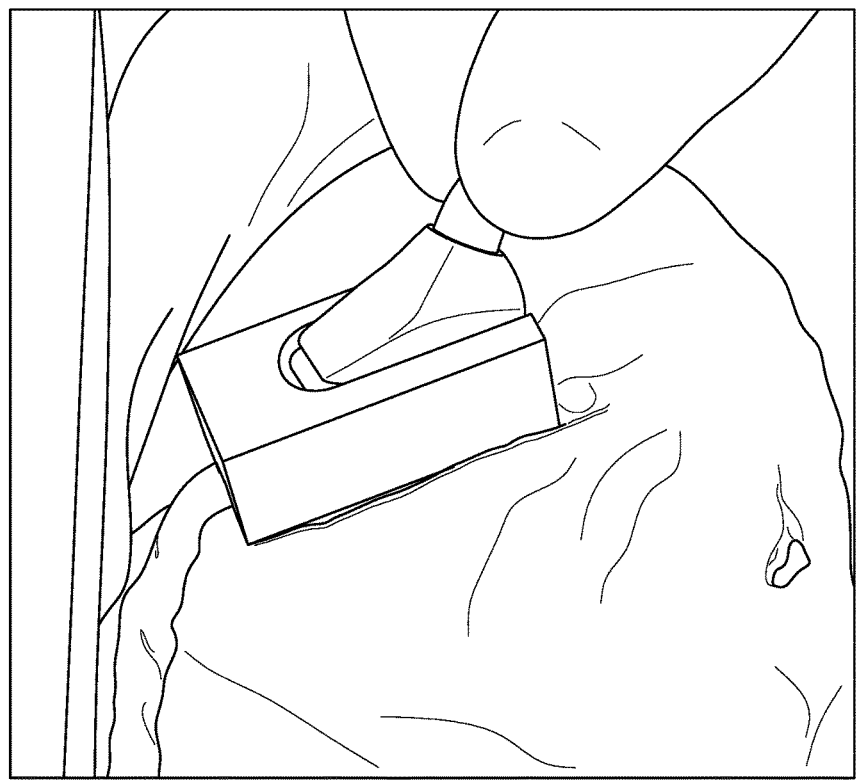
FIG. 10 shows the ultrasound transducer mounted on an embodiment of the device according to the invention, on a LIMA-LAD anastomosis (top), AP-plane (bottom) with an image provided by the probe shown in the lower picture.
Figure 10:
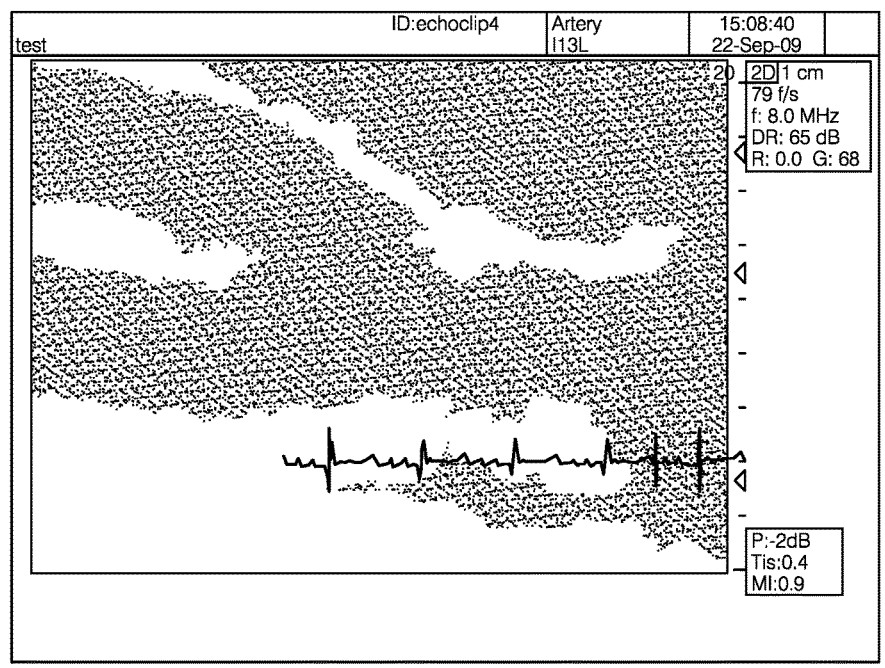
Figure 11:
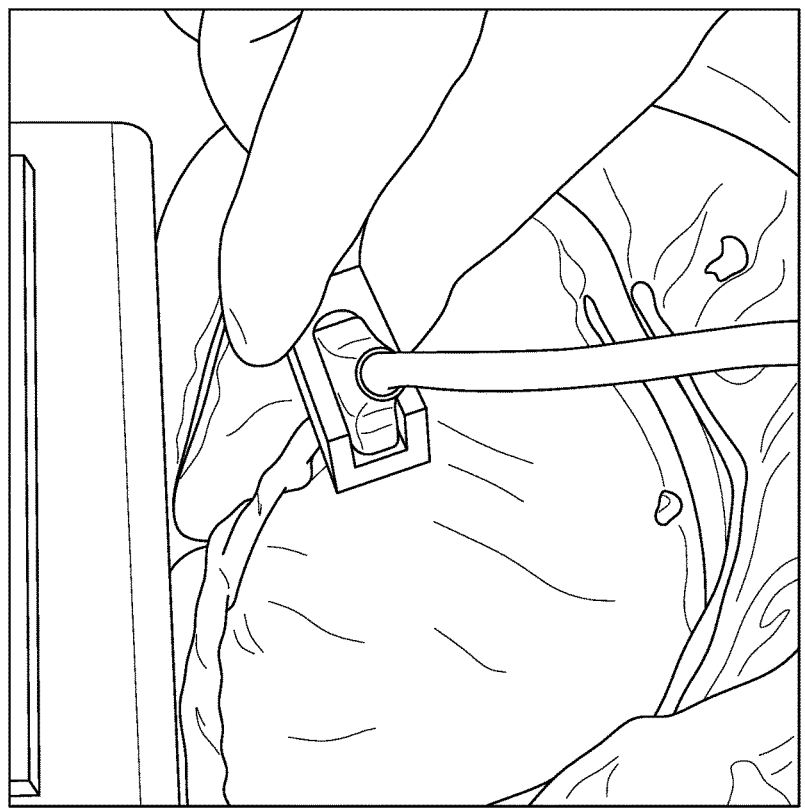
FIG. 11 shows the ultrasound transducer mounted on an embodiment of the device according to the invention, on a LIMA-LAD anastomosis (top), LRplane (bottom) with an image provided by the probe shown in the lower picture. The LR-plane, shown here, is through the middle of the anastomosis.
Figure 11:
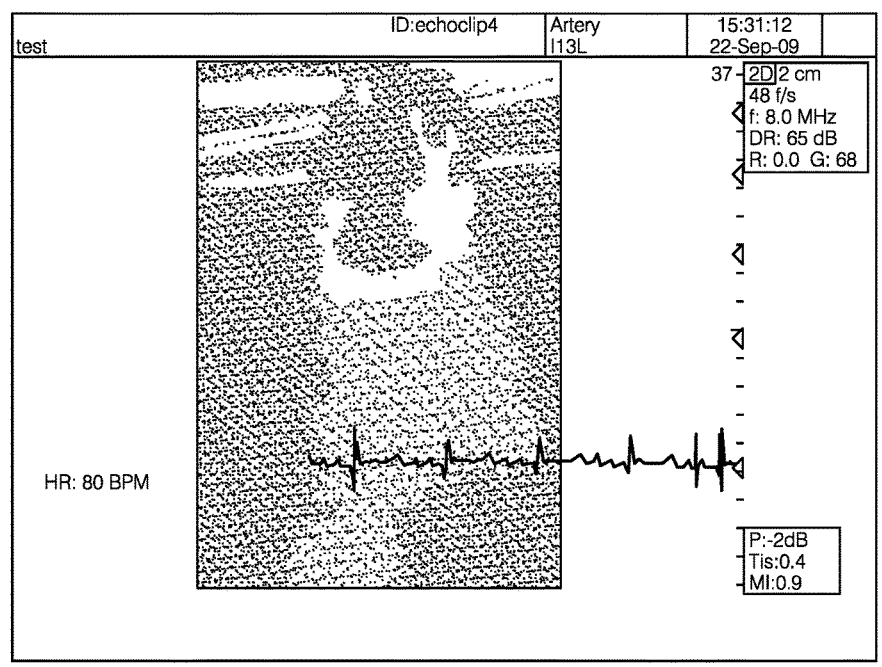

FIGS. 10 and 11 show the device during use. In these specific pictures (top) it is shown how a graft is positioned in the cavity 4 through the opening 6 or 7 according to the invention. Good contact and stabilization (without applying excessive pressure on the graft) is obtained. The bottom pictures in FIGS. 10 and 11 show which image data may be obtained using the device according to the invention.

FIG. 10, top picture, the ultrasound transducer is mounted on a device and placed on a LimaIMA-LAD anastomosis, for visualization of the AP-plane (bottom picture). FIG. 11, top picture, the ultrasound transducer is mounted on the device on a LimaIMA-LAD anastomosis, for visualization of the LR-plane (bottom picture). The LR-plane, shown in FIG. 11, is through the middle of the anastomosis. The device is capable of stabilizing the involved part of the myocardium on beating, and thus pulsating, heart, capable of keeping gel at place and capable of positioning the ultrasound transducer correct for imaging in the anterior-posterior (AP) and left-right (LR) planes without deforming the anastomosis studied.

In FIG. 10 and FIG. 11, the device is used for visualization of the AP- and LR-planes. In FIG. 10, the device is used for visualization of the AP-plane together with a 13 MHz, i13L GE ultrasound transducer (contact area of 27.3 mm by 9.6 mm) especially designed for epicardial imaging. The device with the probe is positioned in a pig model with a LIMA-LAD anastomosis. The transducer is operated by a GE, Vivid 4, echo-machine. In FIG. 11, the transducer is mounted on the device for visualization of the LR plane. For untrained personnel, it takes approximately 10 seconds to visualize the anastomosis in the AP-plane and approximately 15 seconds to obtain the images of the LRplane.

It should be noted that embodiments and features described in the context of one of the aspects of the present invention also apply to the other aspects of the invention. All patent and non-patent references cited in the present application, are hereby incorporated by reference in their entirety.

Embodiments of the invention comprises

A handle 8 for operating the device 10, said handle comprising attachment means for releasable attaching the handle to the device, said attachment means comprising a clip to be fixed to the probe, said clip having at least two gripping members, said at least two gripping members intended for cooperating with corresponding grooves of the probe.

The handle as described above where the handle is provided with at least one of the following conduits from location remote from the device: at least one conduit for passing electronic signal wires from the remote location to the probe, at least one conduit for passing gel from the remote location to the cavity, at least one conduit for passing optical signal wires from a remote location to an optical element connected to the device together with the probe.

A system for examining an organ, said system comprising
a probe,
the device 10, and
the handle 8.

The system as described above, wherein the probe is an ultrasound imaging unit, wherein the cavity of the device is provided with at least two openings for accommodating a graft of a cardiologic by-pass, and where the handle is provided with a clip to be releasable fixed to the probe.

A further aspect of the invention relates to use of the device 10 for providing imaging of a human or animal organ selected from the group of: the heart, coronary veins and/or arteries or other organs exhibiting pulsation or other types of displacement during normal operation of the organ in a human or animal body.

The invention claimed is:

1. A device for supporting an imaging probe away from a portion of a heart bypass graft to reduce pressure on the graft while examining the heart bypass graft, said device comprising:
   a fixation part comprising an aperture configured to receive and secure the imaging probe relative to the device;
   at least two supports for supporting the imaging probe when the imaging probe is positioned in the aperture, the at least two supports having bottom surfaces configured to contact a portion of heart tissue to stabilize the device during examination;
   a cavity extending upward between the supports, the cavity configured to receive at least a part of the graft to be examined, wherein the aperture is positioned above the bottom surfaces of the supports such that the imaging probe is spaced apart from the bottom surfaces and above the part of the graft to be examined when the device is being used together with the imaging probe; and
   at least one opening in one of the at least two supports, the opening exiting in a direction that is parallel to a plane defined by the bottom surface of the supports, the at least one opening in communication with the cavity, wherein the at least one opening is also configured to receive at least a portion the part of the graft to be examined such that the graft can be imaged by the imaging probe without applying pressure on the graft;
   wherein the cavity is oblong with a longitudinal axis of the cavity positioned longitudinally or transversely to an intended direction of displacement of the imaging probe when imaging the bypass graft; and
   wherein the device is capable of holding the imaging probe, by choice of an operator, either in a first direction wherein an imaging plane of the imaging probe is parallel with the oblong cavity or in a second direction wherein an imaging plane of the imaging probe is transverse to the oblong cavity.

2. The device according to claim 1, wherein each of the at least two supports comprises an opening, said openings being provided opposite each other.

3. The device according to claim 1, wherein the at least two supports are positioned parallel to each other with a mutual distance of between 3 mm to 50 mm.

4. A device according to claim 1, wherein the at least two supports have a height between 1 mm and 10 mm, said height being measured from the bottom surface of the supports to a bottom surface of the imaging probe.

5. The device according to claim 1, wherein the cavity is oblong with a longitudinal axis of the cavity positioned longitudinally to an intended direction of displacement of the imaging probe when imaging the bypass graft.

6. The device according to claim 1, wherein the cavity is oblong with a longitudinal axis of the cavity positioned transversely to an intended direction of displacement of the imaging probe when imaging the bypass graft.

7. The device according to claim 1, wherein at least part of the device is transparent to the human eye for enabling locating the device towards the bypass graft.

8. The device according to claim 1, wherein said device is intended for an ultrasonic imaging probe and said device comprises an inlet to the cavity for adding a gel, said inlet being in fluid communication with a reservoir for the gel, said reservoir for the gel being remotely placed in relation to the cavity.

9. The device according to claim 1, wherein a handle is arranged for operating said device when connected to the imaging probe, and wherein said handle is provided with at least one of the following conduits from a location remote from the device: at least one conduit for passing electronic signal wires from the remote location to the imaging probe, at least one conduit for passing gel from the remote location to the cavity, or at least one conduit for passing optical signal wires from a remote location to an optical element connected to the device together with the imaging probe.

10. A device according to claim 1, wherein the aperture further comprises one or more protrusions or notches for holding the imaging probe in the device.

11. The device according to claim 10, wherein the protrusions are one or more beads, or where the notches are one or more grooves, extending along side walls of the device, said side walls forming an aperture of the device.

12. A method for holding an imaging probe selected from the group consisting of: ultrasound imaging equipment and blood flow measuring equipment comprising:
   providing the device of claim 1; and
   holding an imaging probe with said device.

13. A method for providing imaging of a bypass graft comprising:
   providing the device of claim 1; and
   holding an imaging probe from an imaging device steady relative to the device of claim 1; and imaging said bypass graft.

* * * * *